United States Patent
Toyokawa

(10) Patent No.: US 7,824,439 B2
(45) Date of Patent: Nov. 2, 2010

(54) ZIGZAG-SHAPED STENT CONFIGURED TO PRODUCE LESS WALL DAMAGE

(75) Inventor: Yoshihide Toyokawa, Tokyo (JP)

(73) Assignee: Zeon Corporation, Tokyo (JP)

( * ) Notice: Subject to any disclaimer, the term of this patent is extended or adjusted under 35 U.S.C. 154(b) by 122 days.

(21) Appl. No.: 11/630,448

(22) PCT Filed: Jun. 24, 2005

(86) PCT No.: PCT/JP2005/011617

§ 371 (c)(1),
(2), (4) Date: Dec. 21, 2006

(87) PCT Pub. No.: WO2006/001367

PCT Pub. Date: Jan. 5, 2006

(65) Prior Publication Data
US 2008/0046067 A1 Feb. 21, 2008

(30) Foreign Application Priority Data
Jun. 25, 2004 (JP) ............................. 2004-187789

(51) Int. Cl.
A61F 2/06 (2006.01)
(52) U.S. Cl. ..................................... 623/1.16; 623/1.15
(58) Field of Classification Search ....... 623/1.15–1.18, 623/1.1–1.14, 1.19–1.21, 1.34
See application file for complete search history.

(56) References Cited

U.S. PATENT DOCUMENTS

| | | | | |
|---|---|---|---|---|
| 6,464,720 B2 * | 10/2002 | Boatman et al. | ........... | 623/1.15 |
| 6,551,351 B2 * | 4/2003 | Smith et al. | ................ | 623/1.16 |
| 6,743,252 B1 | 6/2004 | Bates et al. | | |
| 6,942,690 B1 * | 9/2005 | Pollock et al. | ............. | 623/1.15 |
| 2001/0001317 A1 * | 5/2001 | Duerig et al. | .............. | 623/1.15 |
| 2002/0007212 A1 * | 1/2002 | Brown et al. | ............... | 623/1.16 |
| 2002/0035395 A1 | 3/2002 | Sugimoto | | |
| 2002/0143386 A1 * | 10/2002 | Davila et al. | ............... | 623/1.15 |
| 2002/0161428 A1 * | 10/2002 | Oepen et al. | ............... | 623/1.15 |
| 2003/0069630 A1 * | 4/2003 | Burgermeister et al. | .... | 623/1.15 |

(Continued)

FOREIGN PATENT DOCUMENTS

JP 2002-000739 A 1/2002

(Continued)

*Primary Examiner*—David Isabella
*Assistant Examiner*—Andrew Iwamaye
(74) *Attorney, Agent, or Firm*—Birch, Stewart, Kolasch & Birch, LLP

(57) ABSTRACT

A stent of interconnected ring-shaped stent units formed by a continuous threadlike material that extends back and forth to form a zigzag pattern of segments extending between opposite side turned edge portions. The zigzag pattern forming the outer circumference of each ring-shaped stent unit with at least some of said turned edge portions at a same side of the segments having a shifted position along the stent axial direction relative to a position of others of said turned edge portions at that same side of the segments so that not all of the adjacent tuned edge portions at that same side of the segments are aligned along a common circle extending around the outer circumference of each ring-shaped stent unit. At least some of the turned edge portions are also formed to have a wider line width than the line width of the segments.

10 Claims, 7 Drawing Sheets

U.S. PATENT DOCUMENTS

| | | |
|---|---|---|
| 2003/0120334 A1 | 6/2003 | Gerberding |
| 2003/0158596 A1 | 8/2003 | Ikeuchi et al. |
| 2004/0015229 A1* | 1/2004 | Fulkerson et al. .......... 623/1.22 |
| 2004/0073291 A1* | 4/2004 | Brown et al. ............... 623/1.15 |
| 2004/0088039 A1* | 5/2004 | Lee et al. .................... 623/1.15 |
| 2004/0093073 A1 | 5/2004 | Lowe et al. |
| 2004/0186550 A1* | 9/2004 | Bonsignore ................ 623/1.15 |
| 2005/0049674 A1* | 3/2005 | Berra et al. ................ 623/1.13 |
| 2005/0096727 A1* | 5/2005 | Allen et al. ................ 623/1.15 |
| 2005/0172471 A1* | 8/2005 | Vietmeier ................... 29/447 |

FOREIGN PATENT DOCUMENTS

| | | |
|---|---|---|
| JP | 2002-095756 A | 4/2002 |
| JP | 2002-530146 A | 9/2002 |
| JP | 2002-532136 A | 10/2002 |
| WO | WO-00/30563 A1 | 6/2000 |
| WO | WO-00/35378 A1 | 6/2000 |
| WO | WO-03/057076 A1 | 7/2003 |
| WO | WO 03/094798 A1 * | 11/2003 |
| WO | WO-03/094798 A1 | 11/2003 |

* cited by examiner

[FIG. 1]
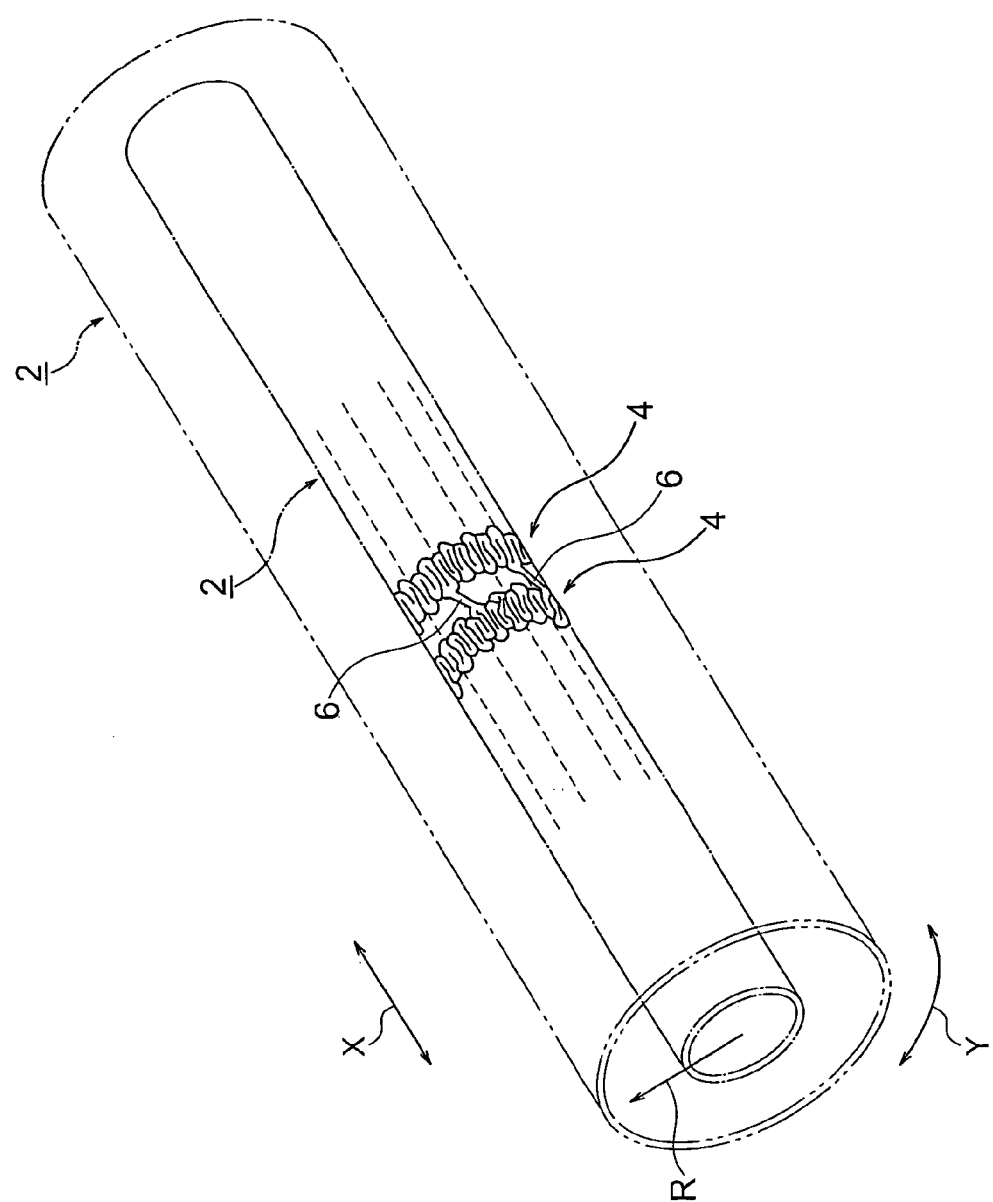

[FIG. 2]
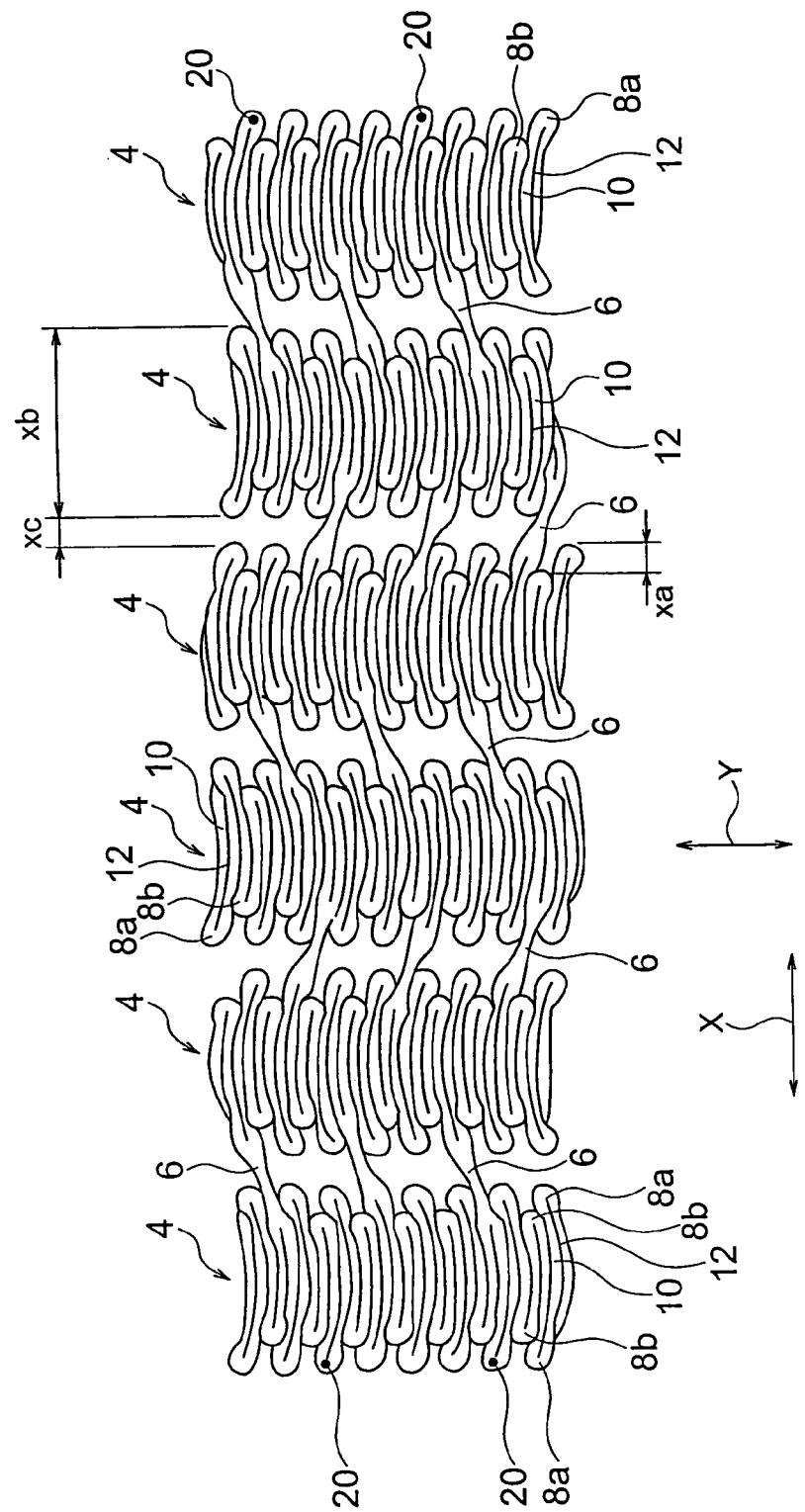

[FIG. 3]
(A)
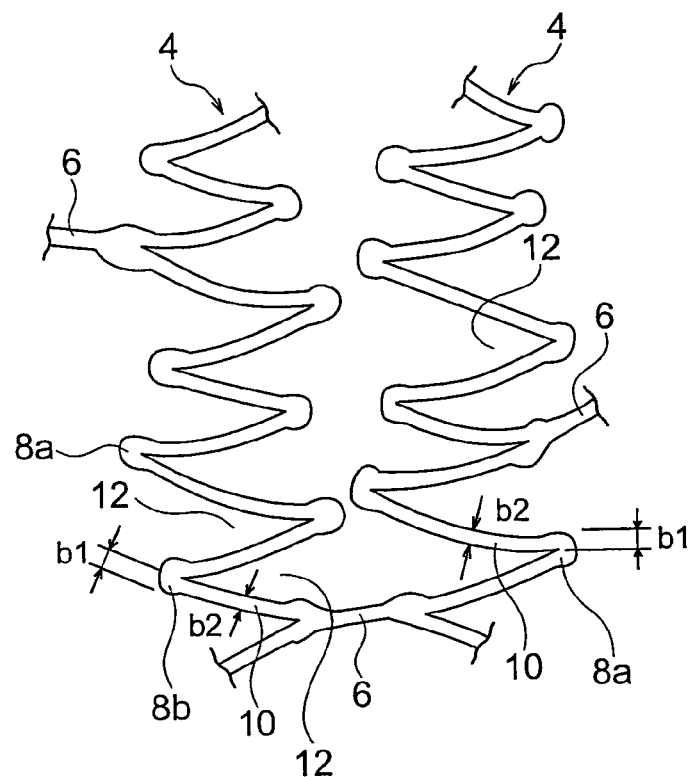
(B)
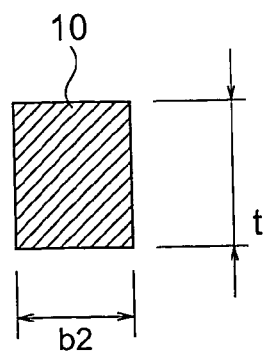

[FIG. 4]
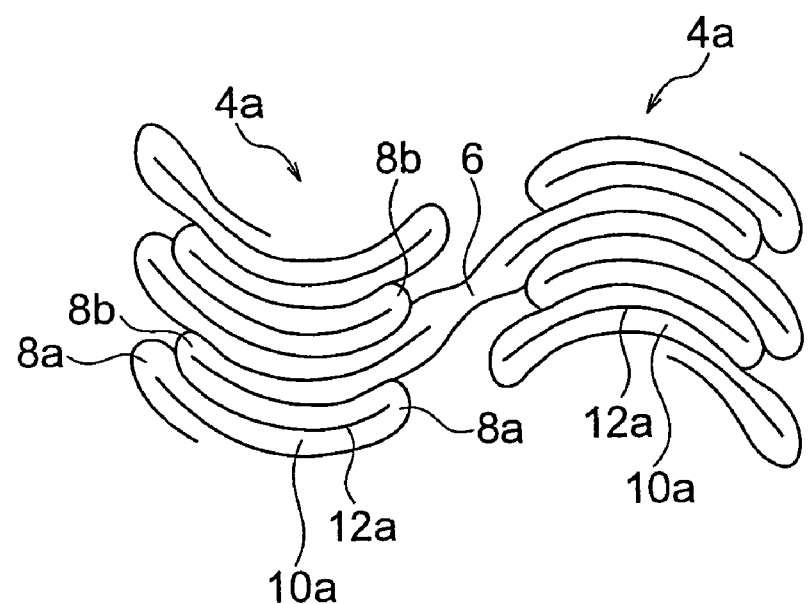

[FIG. 5]
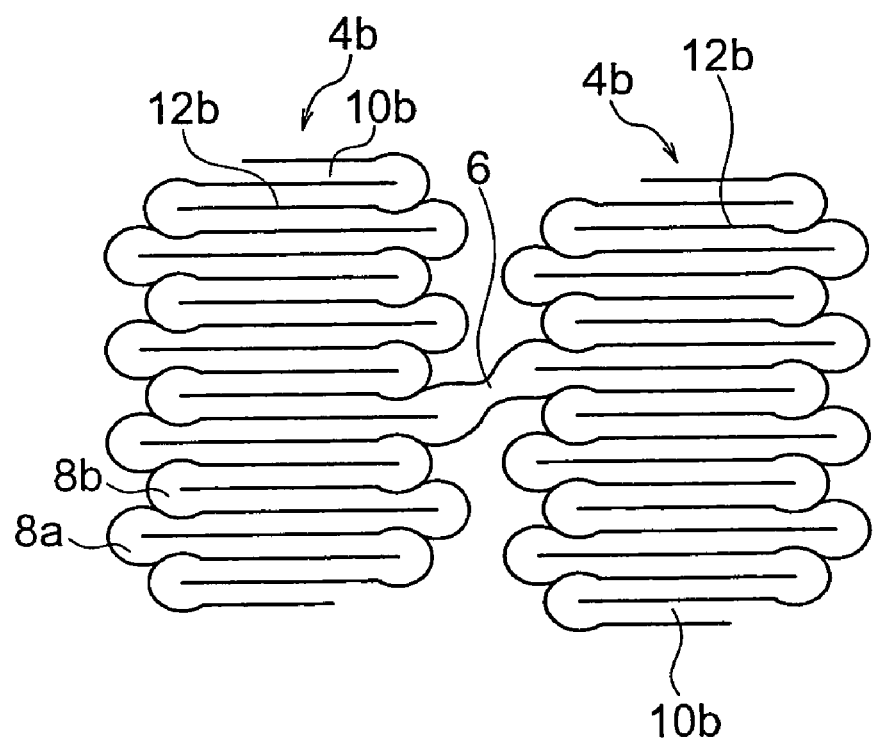

[FIG. 6]
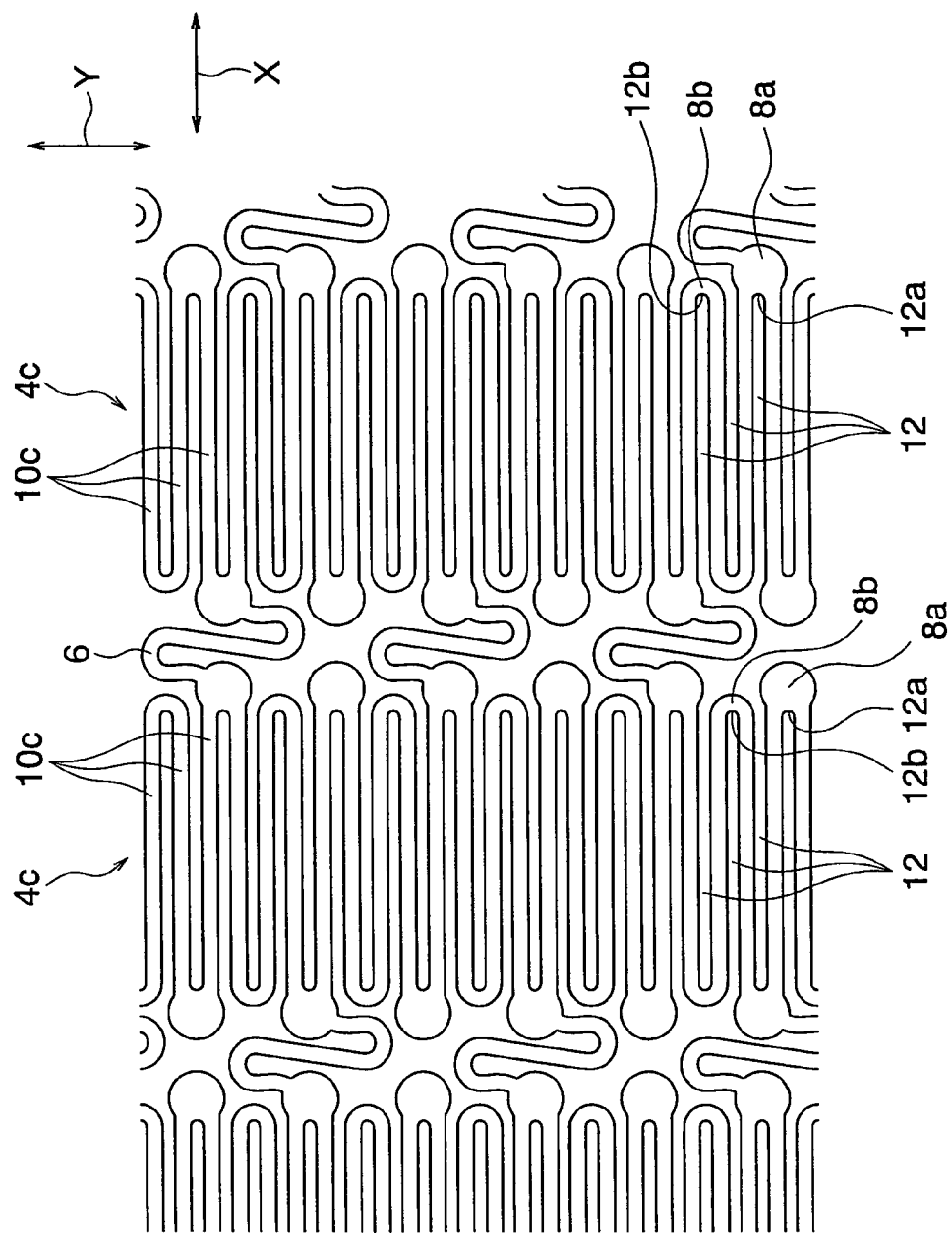

[FIG. 7]
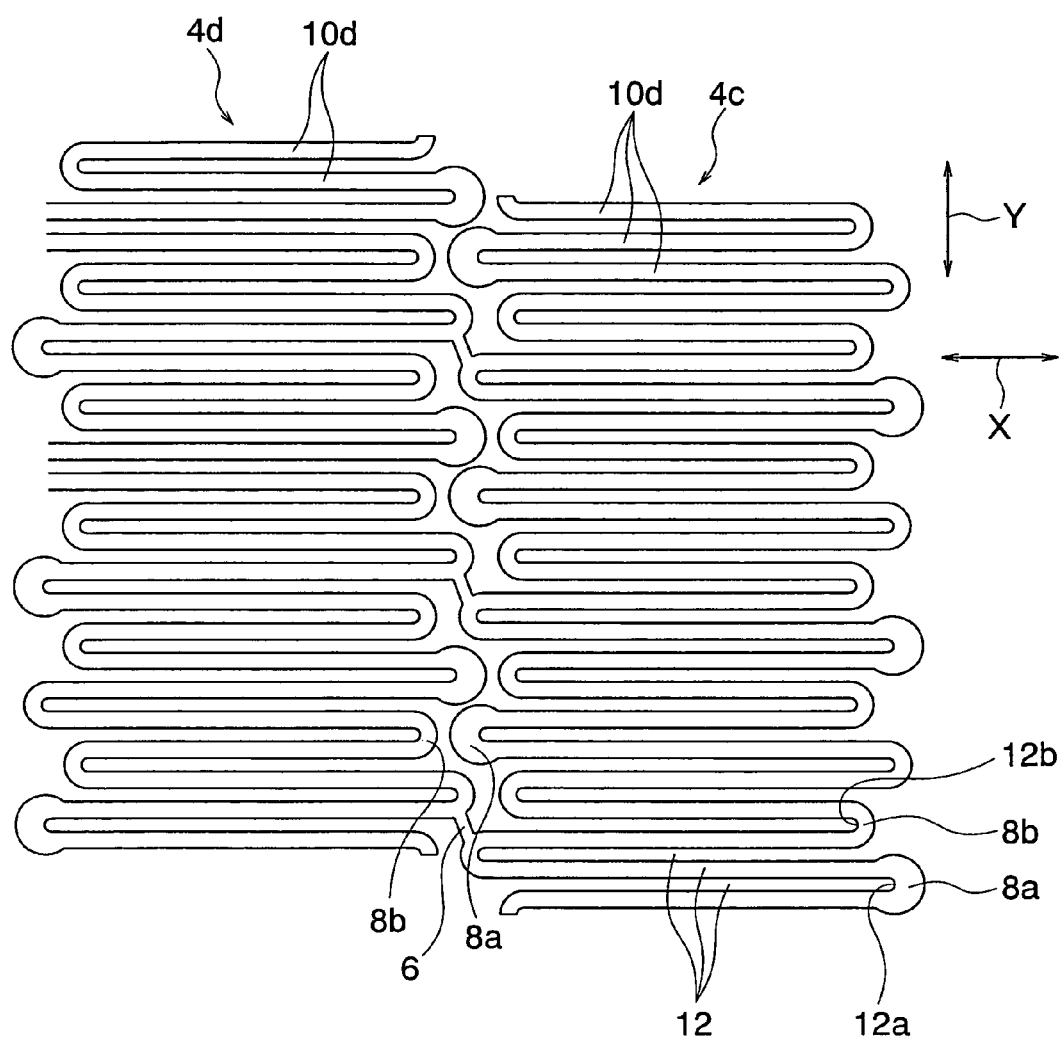

ZIGZAG-SHAPED STENT CONFIGURED TO PRODUCE LESS WALL DAMAGE

TECHNICAL FIELD

The present invention relates to a stent placed at a constricted part for securing a lumen in the human body when a constricted part arises in a lumen in the body, such as a bile duct, blood vessel, trachea, esophagus and urethra.

BACKGROUND ART

When any constricted part arises in a lumen in the body, such as a bile duct, blood vessel, trachea, esophagus and urethra, a medical treatment of placing a stent at the constricted part to secure the lumen in the body has been given. A stent normally has a tube shaped body having an adjustable outer diameter and is inserted to a lumen in the body while the outer diameter is adjusted to be small (a contracted state), positioned at a constricted part, where the outer diameter is made larger (an expanded state), and placed to secure the lumen of the constricted part.

In the stent, it is known that the structure (design) of a tube wall thereof largely affects various capabilities, and variously designed stents have been developed. For example, the patent article 1 discloses a stent, wherein the tube wall is configured by a threadlike material (web pattern) having a zigzag shape formed continuously in the circumferential direction.

The stent in the patent article 1 has excellent flexibility when in a contracted state, so that it can be inserted easily to a lumen in the body, furthermore, the expanded state is easily maintained, so that it has an excellent capability of securing the lumen in the body.

However, the stent in the patent article 1 has a possibility of damaging an inner wall of the lumen in the body by edges of turned edge portions of the zigzag-shaped threadlike material when expanding in the lumen in the body. When a lumen in the body is damaged by a stent, not only damaging the lumen in the body, a phenomenon (ingrowth) that biologic tissue passes through interspaces of the stent and enters into the stent to occlude the lumen in the body is easily caused as well.

Also, in some cases, a film (a cover film) formed by a synthetic resin, etc. is wound when using the stent for a purpose of securing a lumen in the body more surely. However, if a film is wound when using the stent in the patent article, edges of the turned edge portions of the zigzag-shaped threadlike material may stub the film to break the film at the time of expanding in a lumen in the body.

Patent Article 1: The Japanese Patent Publication No. 2002-524135

DISCLOSURE OF THE INVENTION

The present invention was made in consideration of the above circumstances and has as an object thereof to provide a stent having excellent flexibility when in a contracted state, capable of being inserted to a lumen in the body easily and maintaining an expanded state easily and, moreover, having a small possibility of damaging an inner wall in the lumen in the body and a cover film.

To attain the above object, according to a first invention, there is provided a stent, comprising:

ring-shaped stent units formed by zigzag-shaped threadlike material continuously in the circumferential direction and expandable in the radius direction from a contracted state thereof; and a connection portion for connecting at least one of turned edge portions of said zigzag-shaped threadlike material composing said stent units and at least one of the turned edge portions of the zigzag-shaped threadlike material in another unit adjoining to one of said stent units in the axial direction, wherein a plurality of said stent units are connected by said connection portions in the axial direction to form a tubular shape as a whole;

in said stent units in the contracted state, said turned edge portions are disposed in mutual shifted positions toward the stent axial direction from each other between said turned edge portions adjoining to each other in the circumferential direction.

The stent according to the present invention has the configuration that a plurality of ring-shaped stent units are arranged along the axial direction of the stent and the stent units are connected by connection portions, and parts of the connection portions have excellent flexibility, so that relative movement between the stent units is easy. Therefore, it easily bends according to a winding lumen in the body and insertion of the stent to the lumen in the body is easy.

Also, in the stent according to the present invention, an outer diameter of each stent unit can be made large by widening an angle of turned edges between turned edge portions of the zigzag-shaped threadlike material. Namely, the ring-shaped stent unit can be expanded in the radius direction from a contracted state, consequently, an outer diameter of the stent can be made large. Furthermore, when the stent unit expands, the angle of turned edges between turned edge portions of the zigzag-shaped threadlike material is hard to be narrowed by a pressure from the outside of the stent unit and the expanded state of the stent is maintained easily.

Furthermore, in the stent according to the present invention, in the stent unit in a contracted state, positions of the turned edge portions are shifted toward the axial direction of the stent between turned edge portions being adjacent in the circumferential direction. Namely, ends of turned edge portions being adjacent in the circumferential direction are positioned at different coordinates from each other on a coordinate system in the axial direction of the stent. Therefore, even if a line width of the threadlike material positioned at the turned edge portions is made wide or an outer shape of each turned edge portion is made to be rounded, a linear width of the line material at parts other than the turned edge portions can be maintained as narrow as possible. Namely, in the stent according to the present invention, without sacrificing an expansion rate from the contracted state to the expanded state, the turned edge portions can be formed to be a shape for preventing damages on inner walls of a lumen in the body and a cover film.

According to the present invention, it is possible to provide a stent having excellent flexibility when in a contracted state, capable of being inserted to a lumen in the body easily and maintaining an expanded state easily and, moreover, having a small possibility of damaging an inner wall in the lumen in the body and a cover film.

Note that, in the present invention, a shape of a cross section of the threadlike material composing the stent units is not particularly limited and a circular shape, oval shape and rectangular shape, etc. may be mentioned. In terms of simplifying manufacturing, the shape of a cross section of the threadlike material is preferably rectangular.

Preferably, a position shift amount between the turned edge portions adjoining to each other in the circumferential direction at positions shifted from each other toward an axial direction of the stent is 1.2 to 20 times and more preferably 1.5 to 5 times as large as a line width of the threadlike material at the turned edge portions. When the position shift amount is too small or too large, the effects of the present invention are liable to be reduced.

Preferably, positions of the turned edge portions are arranged to be shifted along the circumferential direction and alternately in the opposite axial directions. Also preferably, alternating turned edge portions in the circumferential direction are positioned at the same positioning the axial direction. When configured as such, the effects of the present invention are enhanced.

Preferably, exterior of the turned edge portion is rounded. Also preferably, a line width of the threadlike material at least a part of the turned edge portions is wider than a line width of the threadlike material at portions other than the turned edge parts. By widening the line width of the threadlike material positioned at the turned edge portions and making the outer shape of the turned edge portions rounded, a possibility of damaging an inner wall of a lumen in the body and a cover film by edges of the turned edge portions becomes low at the time of expanding the stent unit. Also, by widening the line width of the threadlike material positioned at the turned edge portions and making the outer shape of the turned edge portions rounded, strength of the turned edge portions can be improved. As a result, an angle of turned edges between the turned edge portions of the threadlike material is furthermore hard to be narrowed even by a pressure from the outside of the stent unit and an expanded state of the stent is furthermore easily maintained.

Preferably, turned edge portions having a wide line width are arranged at intervals along the circumferential direction between turned edge portions having substantially the same line width as a line width of the threadlike material at parts other than the turned edge portions.

In that case, preferably, end positions of slits for forming turned edge portions having a wide line width in each of the stent units and end positions of slits of turned edge portions having substantially the same line width as a line width of the threadlike material at parts other than the turned edge portions are at substantially the same position in the axial direction of the stent.

In that case, in each of the stent units, end positions of the slits are at the same position in the stent axial direction, so that lengths of the slits can be unified along the circumferential direction and it is easy to uniformly expand the stent. Also, in turned edge portions having a wide line width and turned edge portions having substantially the same line width as a line width of the threadlike material at parts other than the turned edge portions, end positions thereof are shifted from each other toward the stent axial direction, so that basic effects of the present invention can be obtained.

Furthermore, due to an existence of the turned edge portions having a wide line width, a possibility of damaging an inner wall of a lumen in the body and a cover film by edges of the turned edge portions becomes low. Also, from the same reason, strength of the turned end portions can be improved.

Alternately, end positions of slits for forming turned edge portions having a wide line width in each of the stent units and end positions of slits of turned edge portions having substantially the same line width as a line width of the threadlike material at parts other than the turned edge portions may be shifted from each other toward the axial direction of the stent.

Preferably, a part of the turned edge portions in the stent unit in a contracted state is positioned at a clearance formed and extending along the circumferential direction between two turned edge portions in another stent unit being adjacent to the stent unit in the axial direction.

Preferably, a contrast marker is formed on any one of turned edge portions on the axial end side in the stent unit positioned at an end portion of the stent in the axial direction. At the turned edge portions of the stent of the present invention, a line width of the threadlike material can be made wide, consequently, by forming markers on that part, large markers can be formed. As a result, a stent position can be easily confirmed by radioscopy. Also, an operation of forming markers becomes easy.

Preferably, a shape of the threadlike material connecting the turned edge portions is a curve shape or a sharply bent shape. According to the embodiment, a phenomenon that an entire length of the stent becomes short (shortening) when expanding the stent can be effectively prevented.

Preferably, the connection portion has a straight line shape, a curve shape or a sharply bent shape. A shape of the connection portion is not particularly limited and may be variously embodied.

In the stent according to the present invention, preferably, the entire outer circumference is covered with a cover film. Use of the stent according to the present invention is not particularly limited and it may be used for securing a lumen in the body, such as a bile duct, blood vessel, trachea, esophagus and urethra. Among them, it is preferable to use the stent according to the present invention to secure a lumen of a bile duct having many winding and branching, where the inner wall is easily damaged by conventional stents.

BRIEF DESCRIPTION OF DRAWINGS

FIG. 1 is a schematic perspective view of a stent according to an embodiment of the present invention.

FIG. 2 is a plan view showing a tube wall of the stent shown in FIG. 1 in a contracted state.

FIG. 3A is a plan view of a key part of the stent shown in FIG. 2 in an expanded state, and FIG. 3B is a cross sectional view of a threadlike material of the stent.

FIG. 4 is a plan view of a key part showing as a plane a tube wall of a stent in a contracted state according to another embodiment of the present invention.

FIG. 5 is a plan view of a key part showing as a plane a tube wall of a stent in a contracted state according to still another embodiment of the present invention.

FIG. 6 is a plan view of a key part showing as a plane a tube wall of a stent in a contracted state according to still another embodiment of the present invention.

FIG. 7 is a plan view of a key part showing as a plane a tube wall of a stent in a contracted state according to still another embodiment of the present invention.

BEST MODE FOR CARRYING OUT THE INVENTION

Below, the present invention will be explained based on embodiments shown in the drawings.

First Embodiment

As shown in FIG. 1 and FIG. 2, a stent 2 according to an embodiment of the present invention is configured by a zigzag-shaped threadlike material 10 formed continuously in the circumferential direction Y and has ring-shaped stent units 4 capable of expanding in the radius direction R from a contracted state. The plurality of stent units 4 arranged in the axial direction X are connected with adjacent stent units 4 by connection portions 6 formed to be one body with the threadlike material 10 of the stent units 4 so as to form a tube-shaped stent 2 as a whole.

The threadlike material 10 is, as shown in FIG. 2 and FIG. 3A, bent at turned edge portions 8a and 8b to configure a zigzag shape (zigzag pattern). Slits 12 are formed between adjoining threadlike material 10 bent at the turned edge portions 8a and 8b. In FIG. 2, the slits 12 are closed and the stent units 4 are in a contracted state, while in FIG. 3A, the slits 12 are open and the stent units 4 are in an expanded state.

When the stent units 4 are in a contracted state, the stent 2 is also in a contracted state as a whole. The state is shown by a chain line in FIG. 1. While, when the stent units 4 are in an expanded state, the stent 2 is also in an expanded state as a whole, and the state is shown in by a two-dot chain line in FIG. 1.

In the present embodiment, in the stent units 4 in a contracted state, the turned edge portions 8a and 8b of the threadlike material 10 composing the ring-shaped stent units 4 are positioned by being shifted along the axial direction X of the stent 2 between adjacent turned edge portions in the circumferential direction. Namely, ends of turned edge portions being adjacent in the circumferential direction are positioned at different coordinates from each other on a coordinate system toward the axial direction of the stent. Moreover, the turned edge portions 8a and 8b are disposed in mutual shifted positions alternately toward the opposite axial directions X along the circumferential direction Y, and alternating turned edge portions 8a or 8b in the circumferential direction are positioned at the same position toward the axial direction X. Namely, one protruding side turned edge portion 8a protrudes in the axial direction X with respect to a receding side turned edge portion 8b being adjacent in the circumferential direction Y, and respective protruding side turned edge portions 8a or receding side turned edge portions 8b in a stent unit 4 are at the same position toward the axial direction X.

A shifting amount "xa" between positions of a protruding side turned edge portion 8a and a receding side turned edge portion 8b next to each other (refer to FIG. 2) is preferably 1.2 to 20 times and more preferably 1.5 to 5 times as wide as a line width b1 of the threadlike material 10 at each of the turned edge portions 8a and 8b (refer to FIG. 3A).

Also, in the present embodiment, the line width b1 of the threadlike material 10 at each of the turned edge portions 8a and 8b is wider than a line width b2 of the line material 10 at parts other than the turned edge portions and is preferably 1.1 to 10 times and more preferably 1.2 to 5 times as wide as the line width b2. An outer side of each of the turned edge portions 8a and 8b is rounded, and the curvature radius is approximately the same as that of the line width b1 of the line material 10 at the turned edge portions 8a and 8b and preferably 0.15 to 0.7 mm.

The number of turned edge portions 8a and 8b in each stent unit 4 is not particularly limited, but is preferably 6 to 108 and more preferably 8 to 64 in total per full circle. The "in total per full circle" corresponds to the number of times that the threadlike material is bent per full circle.

A cross sectional face of the threadlike material 10 in the present embodiment is, as shown in FIG. 3B, a rectangular section, and the thickness "t" is preferably 0.1 to 0.4 mm and more preferably 0.15 to 0.35 mm. A line width b2 of the threadlike material 10 is not particularly limited but preferably 0.08 to 0.3 mm and more preferably 0.10 to 0.25 mm.

Note that a line width of the connection part 6 is normally the same as or wider than the line width b2 of the threadlike material 10, preferably 0.1 to 0.4 mm and more preferably 0.15 to 0.30 mm. A thickness of the connection portion 6 is approximately the same as the thickness of the threadlike material 10. The connection portion 6 is formed, as shown in FIG. 2, to connect a protruding side turned edge portion 8a and a receding side turned edge portion 8b in stent units 4 adjacent in the axial direction X to make them to be one body. The connection portions 6 are arranged at predetermined intervals in the circumferential direction Y, and there are preferably 1 to 20 turned edge portions 8a and 8b between connection portions 6 being adjacent in the circumferential direction Y.

As shown in FIG. 2, a length "xb" of each stent unit 4 in the axial direction in a contracted state is not particularly limited but is preferably 2 to 5 mm. Note that the length "xb" of each stent unit 4 in the axial direction is a distance between ends of protruding side turned edge portions 8a and 8a positioned at both end portions in the stent unit 4. Also, a clearance "xc" in the axial direction between stent units 4 being adjacent in the axial direction is not particularly limited but preferably 5 mm or narrower, and particularly preferably 3 mm or narrower. In the present embodiment, the clearance "xc" in the axial direction is a distance between ends of protruding side turned edge portions 8a and 8a being adjacent in the axial direction X. Note that the clearance "xc" in the axial direction may be a negative value as in the later explained fourth embodiment.

An outer diameter of the stent 2 (same as an outer diameter of the stent units 4) in the contracted state is determined in accordance with the use object, etc. and is not particularly limited, but it is preferably 2 to 30 mm, and particularly preferably 4 to 20 mm. The outer diameter of the stent 2 at expansion is 4 to 20 times as large as that at contraction. A length of the entire stent 2 in the axial direction is determined in accordance with the use object, etc. and is not particularly limited, but it is preferably 10 to 300 mm, and particularly preferably 20 to 200 mm.

The stent 2 can be obtained as one body by forming a pattern of the threadlike material 10 and the connection portions 6 by performing, for example, laser processing, electric spark machining, chemical etching and cutting operation on one tube or pipe. A material of the stent 2 is not particularly limited and is formed by a metal or a synthetic resin, etc. It is preferably formed by a metal.

To use the stent 2 as a so-called self expandable stent, it is preferable that the threadlike material 10 and the connection portions 6 composing the stent 2 are formed by a super elastic metal or a shape-memory metal. The super elastic metal and shape-memory metal are not particularly limited and a nickel titanium alloy and a cobalt chrome alloy, etc. may be mentioned. Note that a self expandable stent is a stent able to be shifted from the expanded state to the contracted state due to the elastic deformation and is, for example, pushed into a delivery catheter in a contracted state, pushed out from the delivery catheter in a lumen in the body and expanded.

Alternately, when using the stent 2 as a so-called balloon expandable stent, it is preferable that the threadlike material 10 and the connection portions 6 composing the stent 2 are formed by a metal of plastic deformation. Note that a balloon expandable stent is a stent capable of expanding from a contracted state due to plastic deformation and is expanded by an expanding force of an expanding medical apparatus, such as a balloon catheter, in a lumen in the body.

The entire outer circumference of the stent 2 may be covered with a cover film (not shown). A material of the cover film is not particularly limited and, for example, polybutadiene, polyurethane and styrene elastomer, etc. may be mentioned. By covering around the stent 2 with a cover film, a lumen in the body can be more surely secured.

The stent 2 according to the present embodiment has the configuration that a plurality of ring-shaped stent units 4 are arranged in the axial direction X of the stent 2 and the stent units 4 are connected by connection portions 6, wherein parts of the connection portions 6 have excellent flexibility and the stent units 4 can be easily moved relatively one another. Therefore, it can bend easily according to a winding lumen in the body and insertion of the stent 2 to the lumen in the body is easy.

Also, in the stent 2 according to the present embodiment, as shown in FIG. 3, by making an angle of the slits 12 at the turned edge portions 8a and 8b of the zigzag-shaped threadlike material 10 (a bending angle between the threadlike material 10) wider, each stent unit 4 expands in the circumferential direction Y, consequently, as shown in FIG. 1, an outer diameter of each stent unit 4 can become large in the radius direction R. Namely, the ring-shaped stent unit 4 can expand in the radius direction from the contracted state, consequently, an outer diameter of the stent 2 can become large. Moreover, when the stent unit 4 expands, an angle of the slits 12 is hard to be narrowed by a pressure from the outside of the stent unit 4 and the expanded state of the stent 2 is easily maintained.

Furthermore, in the stent 2 according to the present embodiment, positions of the turned edge portions 8a and 8b are shifted from one another along the axial direction X of the stent 2 between turned edge portions being adjacent in the circumferential direction when the stent unit 4 is in a contracted state. Therefore, even when widening the line width b1 of the threadlike material 10 positioned at the turned edge portions 8a and 8b and making the outer shape of the turned edge portions rounded, the line width b2 of the threadlike material 10 at parts other than the turned edge portions can be maintained as narrow as possible. Therefore, an outer diameter of the stent unit 4 at contraction can become small, an expansion rate from the contracted state to the expanded state can become high, and easiness of insertion of the stent 2 and a capability of securing a lumen in the body become preferable.

By widening the line width b1 of the threadlike material 10 at the turned edge portions 8a and 8b and making the outer shape of the turned edge portions 8a and 8b rounded, a possibility of damaging an inner wall of a lumen in the body and a cover film by edges of the turned edge portions 8a and 8b becomes low. Also, by widening the line width b1 of the threadlike material at the turned edge portions 8a and 8b and making the outer shape of the turned edge portions 8a and 8b rounded, strength of the turned edge portions 8a and 8b can be improved, as well. As a result, an angle of turned edges of the slits 12 between the threadlike material at the turned edge portions 8a and 8b becomes hard to be furthermore narrowed, and the expanded state of the stent 2 is furthermore easily maintained.

Second Embodiment

In the present invention, as shown in FIG. 4, a curvature ratio of a curve shape of the threadlike material 10a and slit 12a connecting the turned edge portions 8a and 8b in each stent unit 4a in a contracted state may be larger than that in the embodiment shown in FIG. 2. Alternately, while not illustrated, the shape of the threadlike material 10a and the slit 12a connecting the turned edge portions 8a and 8b in each stent unit 4a in the contracted state may be a sharply bent shape. Particularly, when the shape of the threadlike material 10a and the slit 12a is a curve shape or a sharply bent shape, a phenomenon that the entire length of the stent 2 in the axial direction becomes short (shortening) at the time of expanding the stent 2 can be effectively prevented.

Note that, in the present invention, when the shape of the threadlike material 10a and the slit 12a connecting the turned edge portions 8a and 8b in each stent unit 4a is made to be a curve shape or a sharply bent shape, it is preferable that convex and concave of the curve shape or sharply bent shape are opposite between stent units 4a being adjacent in the axial direction X. Namely, when a shape of the slit 12a in a stent unit 4a at a position in the axial direction is a convex curve, a shape of the slit 12a in the adjacent stent unit 4a is preferably a concave curve. In the case of the pattern combination as above, particularly, shortening can be effectively prevented.

Also, in the present invention, as shown in FIG. 5, even when the shape of the threadlike material 10b and the slit 12b connecting the turned edge portions 8a and 8b in each stent unit 4b is made to be a straight line shape, the desired purpose of the present invention can be attained.

Third Embodiment

In this embodiment, as shown in FIG. 6, in each stent unit 4c, protruding side turned edge portions 8a having a wide line width and rounded shape of an approximately circular shape are alternately arranged along the circumferential direction Y between receding side turned edge portions 8b having approximately the same line width as a line width of the threadlike material 10c at parts other than the turned edge portions. Moreover, in the present embodiment, an end position 12a of the slit 12 for forming the protruding side turned edge portion 8a having a wide line width and an end position 12b of the slit 12 of the receding side turned edge portion 8b having substantially the same line width as a line width of the threadlike material (a threadlike material connecting the turned edge portions) 10c at parts other than the turned edge portions are at substantially the same position in the stent axial direction.

Also, in this embodiment, a shape of the connection portion 6 is curved to be an inverted S shape and the elasticity is improved.

In this embodiment, in each stent unit 4c, all of the end positions 12a and 12b of the slits 12 are at the same position in the axial direction, so that lengths of the slits 12 can be unified and it is easy to expand the stent uniformly. Also, end positions of the turned edge portions 8a having a wide line width and the turned edge portions 8b having substantially the same line width as a line width of the threadlike material 10c are shifted from one another along the axial direction of the stent, so that same effects as those in the above embodiments can be obtained.

Furthermore, in the present embodiment, due to an existence of the rounded turned edge portions 8a having a wide line width, a possibility of damaging an inner wall of a lumen in the body and a cover film by edges of the turned edge portions 8a becomes low when expanding the stent units 4c. Moreover, from the same reason, strength of the turned edge portions 8a can be also improved.

In the present embodiment, other configuration and effects are the same as those in the above embodiments, so that an explanation thereon will be omitted.

Fourth Embodiment

In this embodiment, as shown in FIG. 7, in each stent unit 4d, end positions 12a of the slits 12 for forming the protruding side turned edge portions 8a formed by a threadlike material having a wide line width and end positions 12b of the slits 12 at the receding side turned edge portions 8b having substantially the same line width as a line width of the threadlike material (a threadlike material connecting the turned edge portions) 10d at parts other than the turned edge portions are positioned by being shifted from each other in the stent axial direction. Moreover, each of the protruding side turned edge portions 8a in each stent unit 4d is configured to be inserted between a pair of protruding side turned edge portions 8a toward each of the receding side turned edge portions 8b in the adjacent stent unit 4d.

In this embodiment, lengths of the slits 12 repeat short and long alternately along the circumferential direction Y, and a clearance in the axial direction between the turned edge portions 8a and 8b in stent units 4d adjoining to each other along the axial direction X becomes small, so that the stent becomes capable of securing a lumen in the body more effectively. Also, since roundness of the turned edge portions 8a having a wide line width can be made large, a possibility of damaging an inner wall of a lumen in the body and a cover film by edges of the turned edge portions 8a can become low. Moreover, from the same reason, strength of the turned edge portions 8a can be also improved.

In the present embodiment, other configuration and effects are the same as those in the above embodiments, so that an explanation thereon will be omitted.

Other Embodiments

Note that, the present invention is not limited to the above embodiments and may be variously modified within the scope of the present invention.

For example, as shown in FIG. 2, contrast markers 20 may be formed on either of the turned edge portions 8a and 8b on the axial end sides in stent units 4 positioned at ends of the stent 2 in the axial direction. A shape of the contrast markers 20 is not particularly limited, but a plate shape or a column shape is preferable and a disk shape or a cylindrical column is particularly preferable. A size of the markers 20 is not particularly limited, but the outer diameter is preferably 0.2 to 2 mm. The markers 20 are attached at both end portions of the stent 2 at predetermined-intervals at a rate of 1 to 8, preferably, 3 to 5 per full circle.

A method of attaching the markers 20 is not particularly limited and a method below may be mentioned as one example. Namely, holes are formed at both end portions of a tube before being processed to have a predetermined pattern corresponding to the threadlike material 10 and the connection portions 6, a column shaped marker material is inserted through the holes, both ends of the marker material are crushed to be fixed to the tube, then, the tube is processed, and a pattern of the threadlike material and the connection portions 6 are obtained, so that the positions having the marker material fixed thereon come to the turned edge portions 8a. A material of the markers 20 is not particularly limited and radiopaque materials, such as gold, platinum, a platinum iridium alloy, white gold, silver, stainless and alloys of these, may be mentioned.

A line width b1 of the turned edge portions 8a and 8b can be made wide in the stent in the present invention, consequently, by forming markers 20 on that part, large markers 20 can be formed. As a result, a stent position can be easily confirmed by radioscopy. Also, an operation of forming the markers 20 becomes easy.

Also, in the embodiment shown in FIG. 2, the connection portions 6 connect the protruding side turned edge portions 8a and the receding side turned edge portions 8b in stent units 4 next to each other in the axial direction, but the present invention is not limited to that and, as shown in FIG. 4 to FIG. 7, they may connect between the protruding side turned edge portions 8a of adjacent stent units 4. Alternately, the connection portions 6 may connect between receding side turned edge portions 8b of adjacent stent units 4. Among these, it is preferable to provide connection portions 6 for connecting the protruding side end portions 8a.

Also, in the embodiment shown in FIG. 2, the line width b1 is made wide and the outer shape is made rounded at all of the turned edge portions 8a and 8b, but the present invention is not limited to that and, as shown in FIG. 6 and FIG. 7, only the protruding side turned edge portions 8a protruding in the axial direction from turned edge portions on both adjacent sides in the circumferential direction may be shaped as above.

Also, use of the stent according to the present invention is not particularly limited and may be used for securing a lumen in the body, such as a bile duct, blood vessel, trachea, esophagus and urethra. Among them, it is preferable to use the stent according to the present invention to secure a lumen of a bile duct having many winding and branching, where the inner wall is easily damaged by conventional stents.

The invention claimed is:

1. A stent, comprising:
ring-shaped stent units formed by a threadlike material formed continuously in a zigzag pattern that extends back and forth to form segments extending between and connected with opposite side turned edge portions, the zigzag pattern of threadlike material extending in a circumferential direction to form a ring-shaped stent unit with an outer circumference that is expandable in a radius direction of the ring-shaped stent unit from a contracted state thereof to an expanded state thereof; and
a connection portion formed by the threadlike material that connects at least one of the turned edge portions of said zigzag pattern of threadlike material forming one of said stent units and at least one of the turned edge portions of the zigzag pattern of threadlike material forming another stent unit adjacent to the at least one of said stent units in a stent axial direction,
wherein:
a plurality of said stent units are connected by said connection portions in the stent axial direction to form a tubular shape as a whole;
in said stent units in the contracted state, at least some of said turned edge portions at a same side of the segments have a shifted position along the stent axial direction relative to a position of others of said turned edge portions at that same side of the segments along the stent axial direction so that all of the adjacent turned edge portions at that same side of the segments are not aligned along a common circle extending around the outer circumference of each ring-shaped stent unit;
a line width of said threadlike material forming at least some of said turned edge portions is wider than the line width of said threadlike material forming the segments;
the shifted position along the stent axial direction of the at least some of said turned edge portions at a same side of the segments relative to a position of others of said turned edge portions at that same side of the segments along the stent axial direction has a magnitude that is 1.2 to 20 times as large as the line width of said threadlike material at said turned edge portions;
the turned edge portions having the line width wider than a line width of the threadlike material forming the segments are arranged at intervals along the circumferential direction so as to be between turned edge portions having substantially the same line width as a line width of the threadlike material forming the segments;

end positions of slits between the segments with turned edge portions having the line width wider than the line width of said threadlike material forming the segments in each of said stent units and end positions of slits between the threadlike material of the segments with turned edge portions having substantially the same line width as a line width of the threadlike material forming the segments are at substantially the same position in the stent axial direction, and said turned edge portions wider than the other turned edge portions in each of said stent units are formed to be of semi-circular shape on both axial sides of each of the stent units in a state that the wider turned edge portions are arranged between the other turned edge portions along the circumference of the stent units.

2. A stent, comprising:

ring-shaped stent units formed by a threadlike material formed continuously in a zigzag pattern that extends back and forth to form segments extending between and connected with opposite side turned edge portions, the zigzag pattern of threadlike material extending in a circumferential direction to form a ring-shaped stent unit with an outer circumference that is expandable in a radius direction of the ring-shaped stent unit from a contracted state thereof to an expanded state thereof; and a connection portion formed by the threadlike material that connects at least one of the turned edge portions of said zigzag pattern of threadlike material forming one of said stent units and at least one of the turned edge portions of the zigzag pattern of threadlike material forming another stent unit adjacent to the at least one of said stent units in a stent axial direction, wherein:

a plurality of said stent units are connected by said connection portions in the stent axial direction to form a tubular shape as a whole;

in said stent units in the contracted state, at least some of said turned edge portions at a same side of the segments have a shifted position along the stent axial direction relative to a position of others of said turned edge portions at that same side of the segments along the stent axial direction so that all of the adjacent turned edge portions at that same side of the segments are not aligned along a common circle extending around the outer circumference of each ring-shaped stent unit;

a line width of said threadlike material forming at least some of said turned edge portions is wider than the line width of said threadlike material forming the segments;

the shifted position along the stent axial direction of the at least some of said turned edge portions at a same side of the segments relative to a position of others of said turned edge portions at that same side of the segments along the stent axial direction has a magnitude that is 1.2 to 20 times as large as the line width of said threadlike material at said turned edge portions;

the turned edge portions having the line width wider than a line width of the threadlike material forming the segments are arranged at intervals along the circumferential direction so as to be between turned edge portions having substantially the same line width as a line width of the threadlike material forming the segments;

end positions of slits between the segments with turned edge portions having the line width wider than a line width of the threadlike material forming the segments in each of said stent units and end positions of slits between the threadlike material of the segments with turned edge portions having substantially the same line width as a line width of the threadlike material forming the segments are shifted from each other along the stent axial direction, and said turned edge portions wider than the other turned edge portions in each of said stent units are formed to be of semi-circular shape on both axial sides of each of the stent units in a state that the wider turned edge portions are arranged between the other turned edge portions along the circumference of the stent unit.

3. The stent as set forth in claim 2, wherein a part of said turned edge portions of a first stent unit in a contracted state is positioned at a clearance formed and extending along the circumferential direction between two turned edge portions of another stent unit adjacent to the first stent unit in the stent axial direction.

4. The stent as set forth in claim 2, wherein a contrast marker is formed on any one of turned edge portions on a stent axial end side in an end stent unit positioned at an end portion of said stent in the stent axial direction.

5. The stent as set forth in claim 1 or claim 2, wherein the segments connecting said turned edge portions have a curve shape.

6. The stent as set forth in claim 1 or claim 2, wherein said connection portion has a straight line shape, a curve shape or a sharply bent shape.

7. The stent as set forth in claim 1 or claim 2, wherein the entire outer circumference is covered with a cover film.

8. The stent as set forth in claim 1, wherein an exterior side of each of said turned edge portions is rounded and has an approximately circular shape with a curvature radius between 0.15 to 0.7 mm.

9. The stent as set forth in claim 2, wherein an exterior side of each of said turned edge portions is rounded and has an approximately circular shape with a curvature radius between 0.15 to 0.7 mm.

10. The stent as set forth in claim 1, wherein said turned edge portions wider than the other turned edge portions in said stent units are connected by the connection portion with said turned edge portions wider than the other turned edge portions in an adjacent stent unit.

* * * * *